United States Patent [19]

Godfroid et al.

[11] Patent Number: 4,888,338
[45] Date of Patent: Dec. 19, 1989

[54] 5-METHOXY ALKYL AMMONIUM TETRAHYDROFURANS AND TETRAHYDROTHIOPHENES AS ANTI-PAF AGENTS

[75] Inventors: Jean-Jacques Godfroid, Paris; Pierre Braquet, Garches, both of France

[73] Assignee: Societe de Conseils de Recherches et d'Applications Scientifiques (S.C.R.A.S.), France

[21] Appl. No.: 199,939

[22] Filed: May 27, 1988

[30] Foreign Application Priority Data

May 29, 1987 [GB] United Kingdom ............... 8712694

[51] Int. Cl.$^4$ ............... C07D 405/12; C07D 409/12; A61K 31/44
[52] U.S. Cl. .................... 514/336; 514/438; 514/471; 546/283; 546/284; 549/75; 549/491
[58] Field of Search ............... 546/283, 284; 549/78, 549/497, 75, 491, 495; 514/336, 438, 461, 471

[56] References Cited

U.S. PATENT DOCUMENTS 4,567,189 1/1986 Fellner et al. .................. 514/338

OTHER PUBLICATIONS

March, J., Advanced Organic Chemistry, 3rd Ed., Wiley & Sons, (1985), p. 312.

Primary Examiner—Richard A. Schwartz
Assistant Examiner—Richard A. Sharpe
Attorney, Agent, or Firm—Lucas & Just

[57] ABSTRACT

This invention relates to new tetrahydrofurans and tetrahydrothiophenes of the general formula:

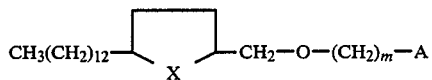

wherein X stands for O or S, m is an integer from 1 to 12 and A is a pyridinium or an ammonium salt, to a preparation process of said compounds and to therapeutic compositions of matter containing the same.

2 Claims, No Drawings

5-METHOXY ALKYL AMMONIUM TETRAHYDROFURANS AND TETRAHYDROTHIOPHENES AS ANTI-PAF AGENTS

The present invention relates to new 5-methoxy alkyl ammonium tetrahydrofurans and tetrahydrothiophenes of the general formula:

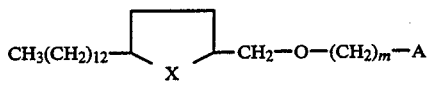

wherein
X stands for O or S,
m is an integer from 1 to 12,
A is:

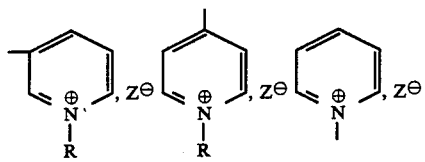

wherein R stands for H or $CH_3$,

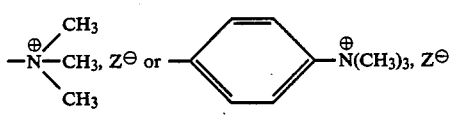

$Z^{\ominus}$ is a pharmaceutically acceptable anion.

The invention relates to these compounds either under the form of their separated stereo-isomers or of any mixture of the same.

These compounds are more particularly interesting as anti PAF agents (PAF means platelets aggregation factor) with the corresponding activity as anti-anaphylactic, anti-thrombotic, anti-ischemic, immunodepressors and acting also against immune alteration of kidney, against various shocks, against skin allergies and intestinal ulcers induced by endotoxine for instance.

The compounds according to the invention may be prepared by reacting a compound of formula I

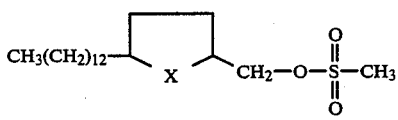

with a compound of formula II

<p align="right">NaOB      II</p> wherein B is the precursor of A containing an amino group or B=A.

The reaction is suitably carried out in solvent such as dimethylformamide at a temperature of 60°–80° C. The conversion from B to A is obtained by usual routes.

The starting materials of formula I may be prepared by reacting a compound of formula III

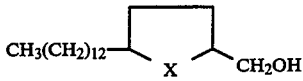

with methane sulfonyl chloride in benzene pyridine followed by classical treatment.

The compound of formula II is prepared by reacting sodium hydride on the corresponding amino alcohol BOH in DMF at 50°–60° C.

EXAMPLE 1

2-(2'-tredecyl tetrahydrofuran-5'-methyloxy) ethyl trimethylammonium iodide

X=O, m=2, A=—$N^{\oplus}$—$(CH_3)_3$, $I^{\ominus}$

Step a: Preparation of 2-tredecyl 5-dimethylamino ethoxy methyl tetrahydrofuran. A=$(CH_2)_2N(CH_3)_2$ To 1,13 g (12.7 mmoles) of dimethylamino ethanol in 100 ml of dry dimethylformamide was added 0.51 g (12.7 mmoles) of NaH (60% dispersion in oil). The mixture was heated 30 minutes at 60° C. with stirring then 2.3 g (6.35 mmoles) of 2-tredecyl tetrahydrofuran 5-methanol methane sulfonate were added. After heating for another 2 hours at 80° C. with stirring, the mixture was cooled and the excess of NaH was decomposed by addition of 5 ml of MeOH. Evaporation of most part of DMF lead to a residue which was diluted with water and extracted three times with diethyl ether. The organic layer was washed with water until neutrality, dried ($MgSO_4$) and evaporated in vacuo. The crude title compound was then purified by chromatography on silica gel using 1 to 5% MeOH in $CHCl_3$ as eluent to yield 0.9 g (40%) as an oil.

IR (film): 2930,2860 (C—H), 2780 (N—$CH_3$), 1120 (C—O—C) $cm^{-1}$, $^1$HNMR (80 MHz, $CDCl_3$, HMDS) δ: 3.95 (m, 2H, CH—O), 3.58 (t, 2H, O$CH_2$—C—N), 3.42 (d, 2H, $CH_2$—O), 2.5 (t, 2H, $CH_2$N), 2.25 (s, 6H, N($CH_3$)$_2$), 2.06–1.35 (m, 6H, $CH_2$—C—O), 1.22 (large s, 22H, ($CH_2$)$_{11}$), 0.82 (t, 3H, $CH_3$).

Step b: Preparation of 2-(2-tredecyl tetrahydrofuran-5 (methyloxy) ethyl trimethylammonium iodide.

0.5 g (1.4 mmoles) of the compound prepared in step (a) above and an excess of methyl iodide (2 g, 14 mmoles) in 50 ml of dry acetone were stirred 2 hours at room temperature. After elimination of the solvent and of the excess of MeI, the residue was chromatographied on a silica gel column using 5% to 20% MeOH in $CHCl_3$ as eluent leading to the title compound as a yellow solid, mp=104° C.

IR (KBr) 2940,2860 (C—H), 1120, 1070 (C—O—C) $cm^{-1}$. $^1$HNMR (80 MHz, $CDCl_3$, HMDS) δ: 4.00 (m, 5H, $CH_2$—O+O—CH—C—O), 3.77 (m, 3H, CH—O+$CH_2$N$^{\oplus}$), 3.56 (s, 9H, $N^{\oplus}$ ($CH_3$)$_3$), 2.25–1.50 (m, 6H, $CH_2$—C—O), 1.25 (large s, 22H, ($CH_2$)$_{11}$), 0.85 (t, 3H, $CH_3$).

EXAMPLE 2

2-(2'-tredecyl tetrahydrofuran 5'-methoxy) tolyl p-trimethylammonium iodide $$X = O, m = 1, A = -\langle\text{phenyl}\rangle-\overset{\oplus}{N}(CH_3)_3, I^{\ominus}$$

The preparation was conducted as in example 1 (a) (b), starting with the same methane sulfonyl compound and p-dimethyl aminobenzyl alcohol prepared by reduction with $NaBH_4$ of commercial p-dimethylaminobenzaldehyde in EtOH to obtain the title compound as a yellow solid, mp=124°-126° C.

IR (KBr): 3000 (aromatic C—H), 2910,2820 (C—H), 1100,1080 (C—O—C) $cm^{-1}$.

$^1$HNMR (80 MHz, $CDCl_3$, HMDS) δ: 8.07 (m, 2H, CH=C—N$^\oplus$), 7.66 (m, 2H, CH=C—C), 4.65 (s, 2H, O—CH$_2$—φ), 4.05 (large s, 11H, N$^\oplus$ (CH$_3$)$_3$+CH—O), 3.49(d, 2H, OCH$_2$—C—O), 2.12-1.42 (m, 6H, CH$_2$—C—O), 1.22 (large s, 22H, (CH$_2$)$_{11}$), 0.82 (t, 3H, CH$_3$).

EXAMPLE 3

(2'-tredecyl tetrahydrofuran-5'-methyloxy) methyl-3 N-methyl pyridinium iodide $$X = O, m = 1, A = \text{[3-N-methylpyridinium with } H_\alpha, H_\beta, H_\gamma, H_\delta\text{], } I^{\ominus}$$

This preparation was conducted as in example 1 (a) (b), starting with the same methane sulfonyl compound and 3-pyridyl methanol to obtain the title compound as a yellow solid. mp: 76° C.

IR (KBr), 3080, 3060 (aromatic C—H), 2940, 2870 (C—H), 1645 (C=N$^\oplus$), 1130, 1080 (C—O—C) $cm^{-1}$.

$^1$HNMR (80 MHr, $CDCl_3$, HMDS) δ: 9.38 (d, 1H, H$_\alpha$), 9.26 (s, 1H, H$_\beta$), 8.57 (d, 1H, H$_\gamma$), 8.17 (t, 1H, H$_\delta$), 4.90 (s, 2H, O—CH$_2$-pyridine), 4.68 (s, 3H, CH$_3$—N$^\oplus$), 4.36-3.72 (m, 2H, CH—O), 3.62 (d, 2H, O—CH$_2$—C—O), 2.21-1.55 (m, 6H, CH$_2$—C—O), 1.25 (large s, 22H, (CH$_2$)$_{11}$), 0.82 (t, 3H, CH$_3$).

EXAMPLE 4

6-(2'-tredecyl tetrahydrofuran-5'-methyloxy) hexyl pyridinium chloride $$X = O, m = 6, A = -\overset{\oplus}{N}\langle\text{pyridinium}\rangle, Cl^{\ominus}$$

Analogous to example 1 starting with the same methane sulfonyl compound and 6-pyridinio hexanol chloride to obtain the title compound as an hygroscopic oil.

$^1$HNMR (80 MHz, $CDCl_3$, HMDS)

δ: 9.55 (d, 2H, CH=$\overset{\oplus}{N}$), 8.55 (m, 1H, $\overset{\oplus}{N}$⟨pyridinium⟩—H), 8.17 (t, 2H, CH=C—N$^\oplus$), 4.97 (m, 2H, CH$_2$N$^\oplus$), 4.47-3.67 (m, 4H, CH—O+O—CH$_2$—C—O), 3.33 (m, 2H, CH$_2$O), 2.2-1.32 (m, 10 H, CH$_2$—C—O+CH$_2$—C—N), 1.2 (large s, 26H, (CH$_2$)$_{11}$+O—C$_2$—(CH$_2$)$_2$—C$_2$—N$^\oplus$), 0.82 (t, 3H, CH$_3$).

TOXICOLOGY

The compounds of the invention have been administered to mice for determination of acute LD$_{50}$. For all the compounds of the invention LD$_{50}$ was over 300 mg/Kg (IP or SC) and 600 mg/Kg (PO).

PHARMACOLOGY

A proof of the pharmaceutical interest of the compounds of the invention has been established by the following pharmaceutical experimentation.

Inhibition of the platelets aggregation on New Zealand rabbits

The experimentation was conducted on platelets with plasma of New Zealand rabbits.

Blood samples were taken from auricular artery and placed in a citrate buffer (3.8%; pH 7.4); blood was further centrifugated for 15 mn at 1200 RPM.

The tested sample was prepared in DMSO, then poured on platelets rich plasma for 1 mn, then a dose of 2.5 nM of PAF was added.

The determination is made on a Cronolog Coultronics apparatus which determines the transmission percentage corresponding to the maximum height of the peak before the desaggregation. The percentage of variation of the inhibition with respect to the transmission percentage is calculated (control: pure DMSO).

This method was described in detail in LABORATORY INVESTIGATIONS, Vol. 41, No. 3, p. 275, 1979, JEAN-PIERRE CAZENAVE, Dr. MED., JACQUES BENZENISTE, Dr. MED., AND J. FRASER MUSTARD, M.D., "Aggregation of Rabbits Platelets by Platelet-Activating Factor Is Independent of the Release Reaction and the Arachidonate Pathway and Inhibited by Membrane-Active Drugs".

The results demonstrate that the compounds inhibit the aggregation induced by 2.5 nM of PAF. Five tests made on 5 different rabbits allowed us to calculate the IC$_{50}$ of the various compounds using the linear regression test.

The values for IC$_{50}$ on platelets have been found as follows:

| | | |
|---|---|---|
| Example 1 | 2.66 | $.10^{-5}$ |
| Example 2 | 1.27 | $.10^{-5}$ |
| Example 3 | 1.1 | $.10^{-5}$ |
| Example 4 | 2.8 | $.10^{-6}$ |

POSOLOGY

The compounds of the present invention can be administered as a therapeutic composition of matter by including an effective amount in an appropriate diluent or carrier.

We claim:

1. A tetrahydrofuran or tetrahydrothiophene of the formula:

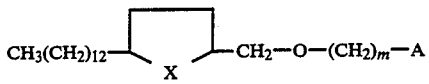

wherein

X stands for O or S, m is an integer from 1 to 12,

A is:

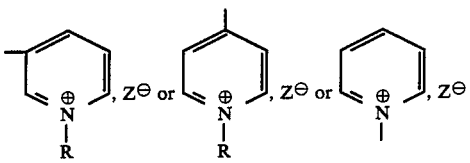

wherein R stands for H or $CH_3$, or

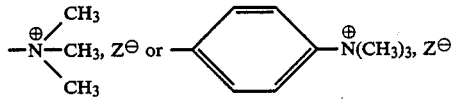

$Z^{\ominus}$ is a pharmaceutically acceptable anion.

2. A therapeutic composition of matter, comprising as an essential ingredient therein, an effective amount of a compound according to claim 1 associated with an appropriate diluent or carrier.

* * * * *

UNITED STATES PATENT AND TRADEMARK OFFICE
CERTIFICATE OF CORRECTION

PATENT NO. : 4,888,338

DATED : December 19, 1989

INVENTOR(S) : Godfroid et al.

It is certified that error appears in the above-identified patent and that said Letters Patent is hereby corrected as shown below:

Column 1, line 20, before the formulae, insert --a pyridinium salt of the formulae:--;
Line 30, before the formulae, insert --an ammonium salt of the formulae:--.

Column 5, last line, insert --a pyridinium salt of the formulae:--.

Column 6, line 11, before the formulae, insert --an ammonium salt of formulae:--.

Signed and Sealed this

Sixteenth Day of October, 1990

Attest:

HARRY F. MANBECK, JR.

Attesting Officer     Commissioner of Patents and Trademarks